United States Patent [19]
Nakashima

[11] Patent Number: 5,135,750
[45] Date of Patent: Aug. 4, 1992

[54] SILICA GELS FOR CONTROLLING INSECT PESTS

[75] Inventor: Yoshito Nakashima, Miyazaki, Japan

[73] Assignee: Fuji-Davison Chemical Ltd., Aichi, Japan

[21] Appl. No.: 666,563

[22] Filed: Mar. 8, 1991

Related U.S. Application Data

[63] Continuation of Ser. No. 326,674, Mar. 21, 1989, abandoned.

[30] Foreign Application Priority Data

Apr. 8, 1988 [JP] Japan ................................. 63-87649

[51] Int. Cl.$^5$ ............................................. A01N 25/34
[52] U.S. Cl. ....................................... 424/407; 424/84; 252/315.6
[58] Field of Search ................ 424/407, 84; 252/315.6

[56] References Cited

U.S. PATENT DOCUMENTS 3,235,451  2/1966  Odeneal ............................... 424/407
4,092,110  5/1978  Adolphin et al. ........... 424/DIG. 11

FOREIGN PATENT DOCUMENTS 57-123277  7/1982  Japan ............................... 252/315.6

OTHER PUBLICATIONS

The 32nd Summary of Lectures at the Japan Applied Zoology and Entomology Institution Conference-1988, Apr. 7-9, Meeting Place D-D34 Yoshito Nakashima, Lethal Effects of Silica Gels on Termites.

Ebeling, W., "Rapid Desiccation of Drywood Termites . . . ", Journal of Economic Entomology, vol. 52, No. 2 (Apr. 1959), pp. 190–207.

Minnick, D. R., et al., "Control of Cryptotermes Brevis", Journal of Economic Entomology, vol. 65, No. 6, (Dec. 1972), pp. 1577–1579.

Sen-Sarma et al., "Bioassay of Silica Aerogel . . . ", Chemical Abstracts, vol. 91, No. 13, Sep. 24, 1979, p. 217, abstract No. 103668g.

Ebeling, W., "Control of the Tropical Rat Mite", Journal of Economic Entomology, vol. 53, No. 3, (Jun. 1960), pp. 475–476.

CA92:99465g Gelled Solid Contg. vol. Active Ingred., Suzuki et al. 23 Jul. 1979, Merck Index, 10th Ed. p. 8325.

Aldrich Catalog, pp. 1149–1151, p. 2148.

Summary of Lectures at the Japan Allied Zoology and Entomology Institution Conference, April 7–9, 1988, Kochi-ken, Japan, pp. 1–5.

Primary Examiner—Lester L. Lee
Attorney, Agent, or Firm—Oliff & Berridge

[57] ABSTRACT

Specific inorganic silica gels are used as an adsorbent drying agent for controlling insect pests in a structure. When it is too humid in the structure, the silica gels adsorb moisture. On the other hand, when it is too dry in the structure, the silica gels supply moisture. The silica gels thus create the environment where household insect pests cannot survive. Moreover, by exposing invading insect pests to silica-gel particles, the pests' tissues are physiologically decayed, and the population density of the insect pests is decreased. Insect pests in the structure can by thus controlled using the silica gels.

1 Claim, 11 Drawing Sheets

SILICA GELS FOR CONTROLLING INSECT PESTS

This is a continuation of application Ser. No. 07/326,674 filed Mar. 21, 1989 and now abandoned.

BACKGROUND OF THE INVENTION

This invention relates to an innovative pest control agent and its usage.

Insect pests cause considerable economic damage to people. However, insect pests are also species of insects. Insects play important roles in the economy of nature. We must consider methods for controlling insect pests to decrease the economic damage they cause without destroying the natural world.

Insect pests such as termites cause economic damage to artificial structures. The amount of the damage is equivalent to that caused by a fire. Termite damage was once limited to wooden structures. However, as man's culture develops and man's living conditions change, the damage extends to new building materials, reinforced concrete structures, transmission cables and telecommunication cables. As a countermeasure, we rely on chemical agents. Various termite-proofing agents are available on the market.

Household insect pests such as termites, ticks, fleas and moths rapidly proliferate, causing economic damage and mental stress to people. When structures are infested with these insects, insect-control and preventive measures must be immediately taken.

The measures depend on the chemical pest control agents available on the market. The agents contain inorganic compounds (e.g. arsenic, boron, molybdenum) and organic compound (e.g. phosphorus, synthetic pyrethrin, IPWC). Certain chemical pest control agents are poisonous to people, and harmful to the environment. The workers at insect pest control companies and the inhabitants in the structure where the control agents have been applied worry about their health.

SUMMARY OF THE INVENTION

In the present invention, specific nontoxic silica gels are used as substitutes for the poisonous and polluting chemical agents used to prevent household insect pests from rapidly developing large populations. By applying the silica gels to the structures constructed with new building materials, the humidity in the structures is controlled to maintain a comfortable environment for people.

The present invention provides silica gels for sticking to, absorbing moisture from, and killing insect pests, comprising at least 0.05% by weight of silica-gel particles with a diameter of 50$\mu$m maximum.

BRIEF DESCRIPTION OF THE DRAWINGS

The invention may be best understood by referring to the following description of the preferred embodiment and the drawings in which.

EMBODIMENT

Figure 1:
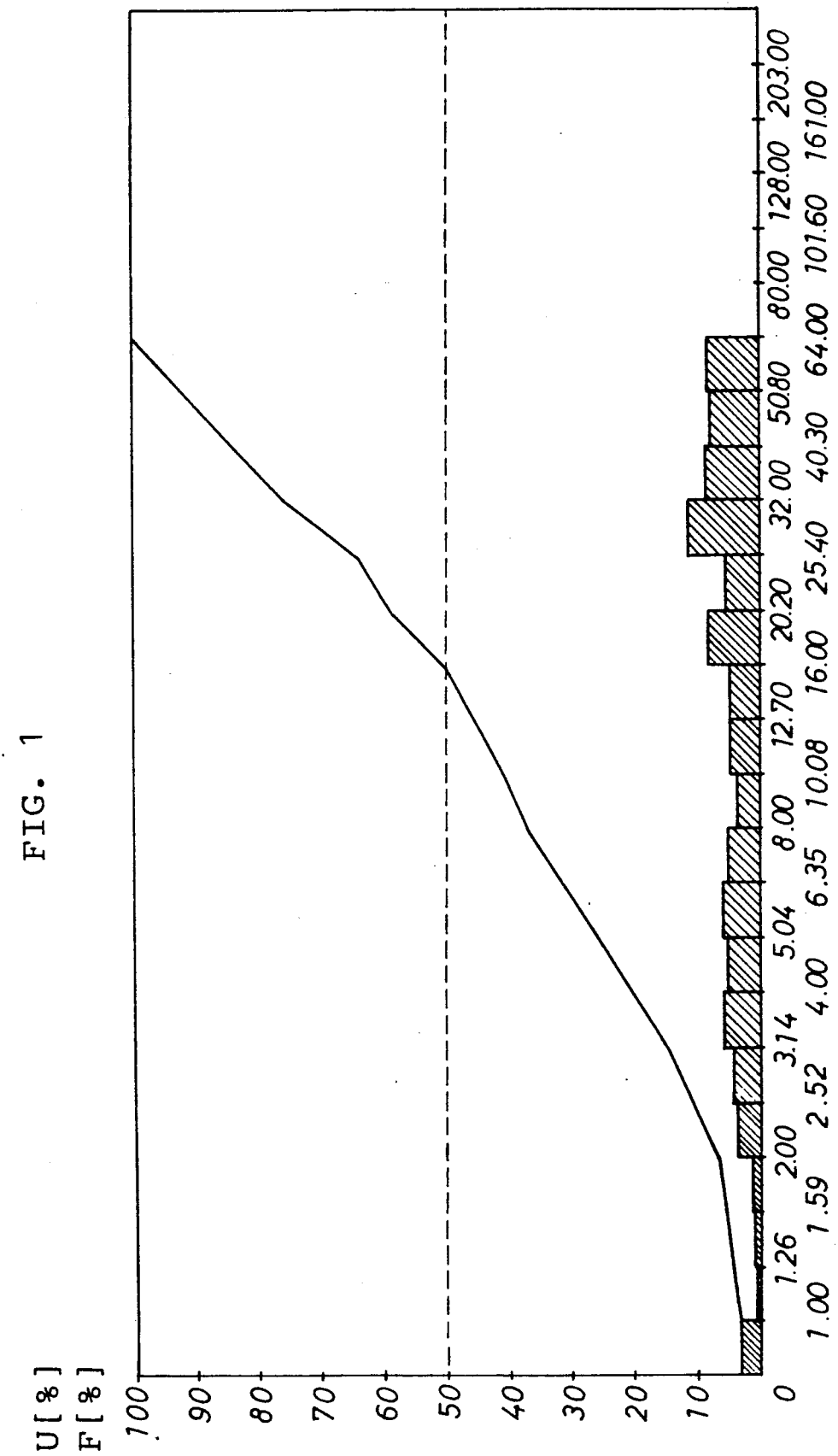
FIG. 1 is a distribution graph of silica-gel particle diameter, in which a bar chart shows the percentage by volume of particles of silica gel by particle diameter and a polygon shows the relationship between the percentage by volume of the particles in the silica gel and the particle diameter.

It is usually so humid, for example, under the floor of wooden structures that dew condenses and insect pests such as termites invade and proliferate. To control these insect pests, polyethylene film is first laid on the ground. Subsequently, silica gels containing at least 0.05% by weight of particles with a diameter of 50$\mu$m or less are sprayed evenly over the film at a rate of 3kg/m$^2$. The humidity under the floor is kept between 65% and 75% on average by the silica gels throughout the year. Insect pests can thus be controlled because the insect pests such as reticulitermes prefer more humid zones. By exposing invading insect pests to the sprayed silica gels, fine particles with a diameter of 50$\mu$m or less of the silica gels stick to the surface of the pests' body. The pests' tissues to which the silica-gel particles stick gradually decay, die and rot. As shown in FIG. 1, the diameter of the silica-gel particles should be 50$\mu$m maximum, preferably 10$\mu$m maximum, and 5$\mu$m maximum is best. The stricken insect pests or other pests cut the rotten tissues away. As time passes, the number of dead pests increases. The lethal effect of the silica-gel particles is limited to individual pests. The pests do not carry the lethal effects of the silica-gel particles to other pests. When the insect pests walk on or become exposed to the surface of the silica gels for sixty to ninety minutes, they die. By spraying the biotically-nontoxic silica gels in the structures, the invading insect pests can be controlled.

To obtain maximum lethal effect, the percentage of the particles with a diameter of 5$\mu$m maximum contained in the silica gels should be 0.05% minimum, preferably 1% minimum, and 2% minimum is best. However, when the silica gels contain too many fine particles with a diameter of 5$\mu$m maximum, the particles disperse in the air, inhibiting the silica gels from being sprayed evenly over the floor. Thus, the percentage of the particles on the silica gels should be 5% maximum. Specifically, the diameter of the silica gels (Home gel) is 350$\mu$m minimum. The silica gels control insect pests by controlling humidity in the structure. Each of the silica gels are covered with the particles. The particles are prepared by filtering the silica gels with a 50$\mu$m filter. The silica gels should contain 5% maximum by weight of the particles. The insect pests die by being exposed to the particles.

The lethal effect of the present embodiment is now explained referring to the graphs.

Figure 2:
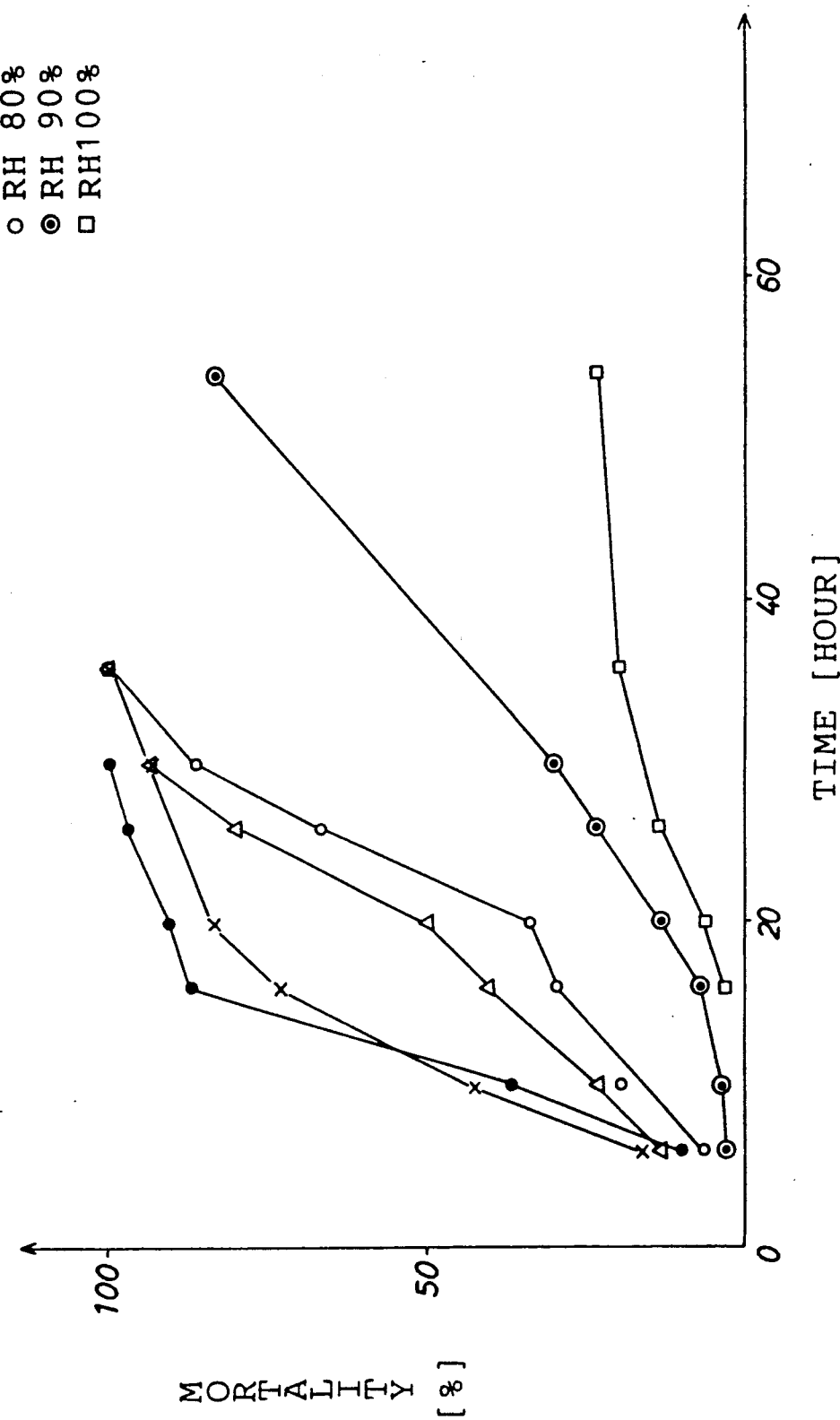
FIG. 2 is a graph showing the relationship between the mortality of reticulitermes and time at various relative humidity levels.
Figure 3:
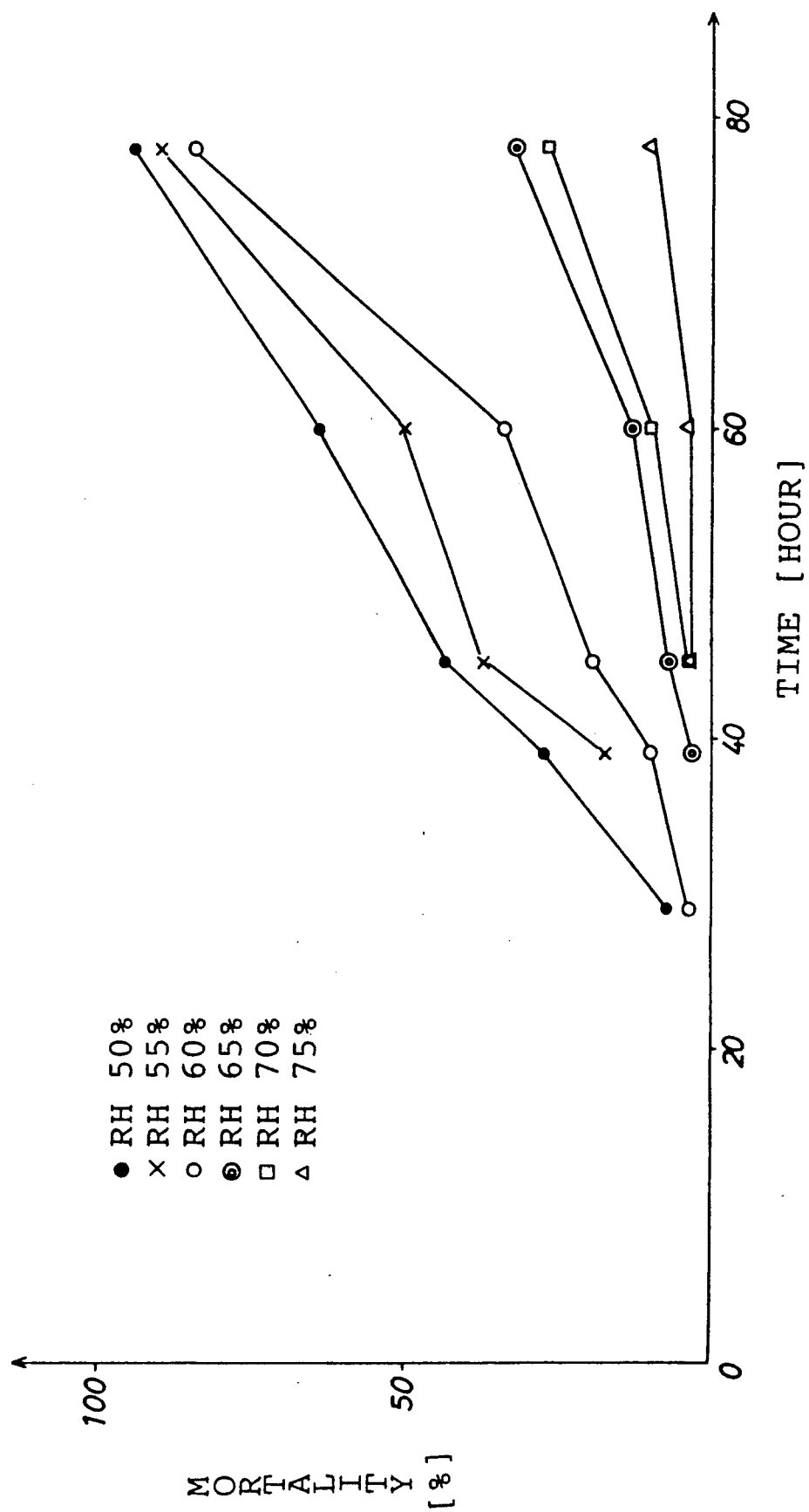
FIG. 3 is a graph showing the relationship between the mortality of coptotermes and time at various relative humidity levels.

As shown in FIG. 2, when the relative humidity in the structure is adjusted to between 50% and 100% using humidity-controlling silica gels, reticulitermes can live only for forty hours at a maximum relative humidity of 80%. As shown in FIG. 3, coptotermes are brought to death or dehydrated at a maximum relative humidity of 60% within eighty hours. In both cases, termites cannot live long, because the silica gels adjusts the relative humidity.

An adsorbent drying agent adsorbs moisture faster than wood. The adsorbent drying agent can create the environment improper for the invasion or the infestation of insect pests. By adjusting the relative humidity with the adsorbent drying agent, termites can be brought to death quickly.

Figure 9:
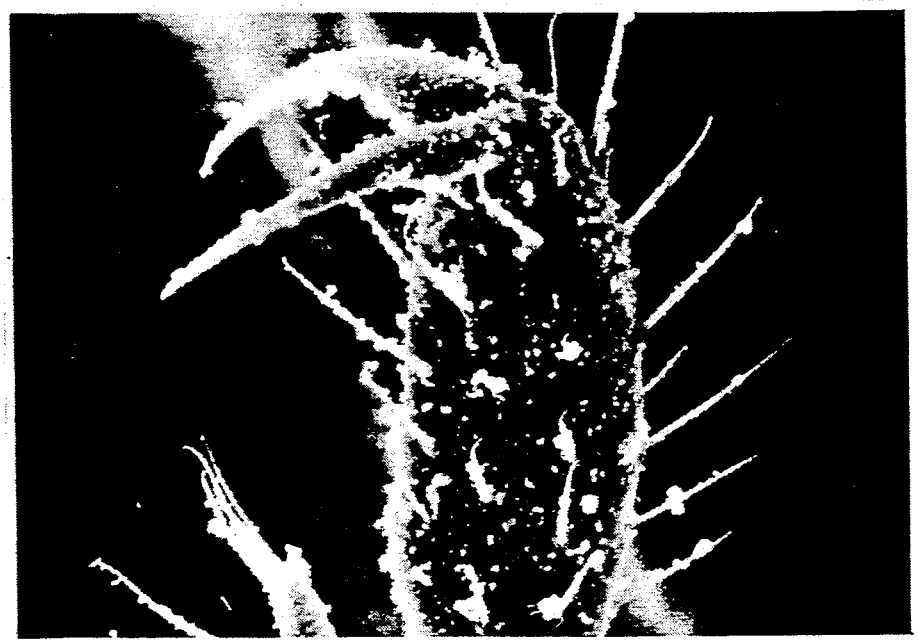

In this embodiment, the minute silica-gel particles with a diameter of 50μm maximum stick to the surface of the termites' body. The particles with the diameter greater than 50μm do not adhere to the surface of the termites' body. In FIG. 9, the particles which seem large are coagulated silica-gel particles. The silica-gel particles partially dehydrate the termites where the silica-gel particles stick to their tissues. The termites die with their tissues decayed by the silica-gel particles.

Figure 4:
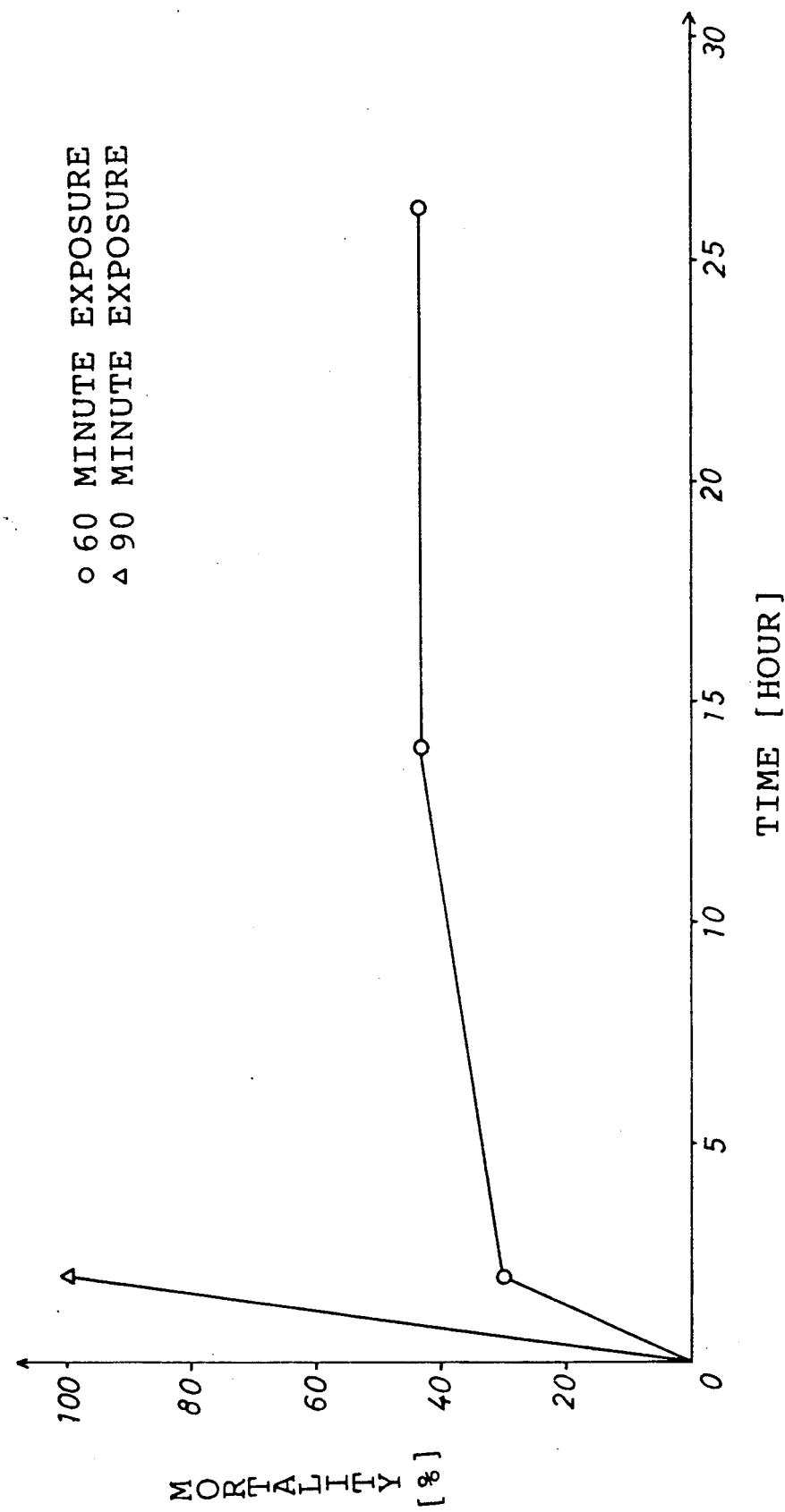
FIG. 4 is a graph showing the relationship between the mortality of reticulitermes and time after the exposure of the reticulitermes to Home gels.
Figure 5:
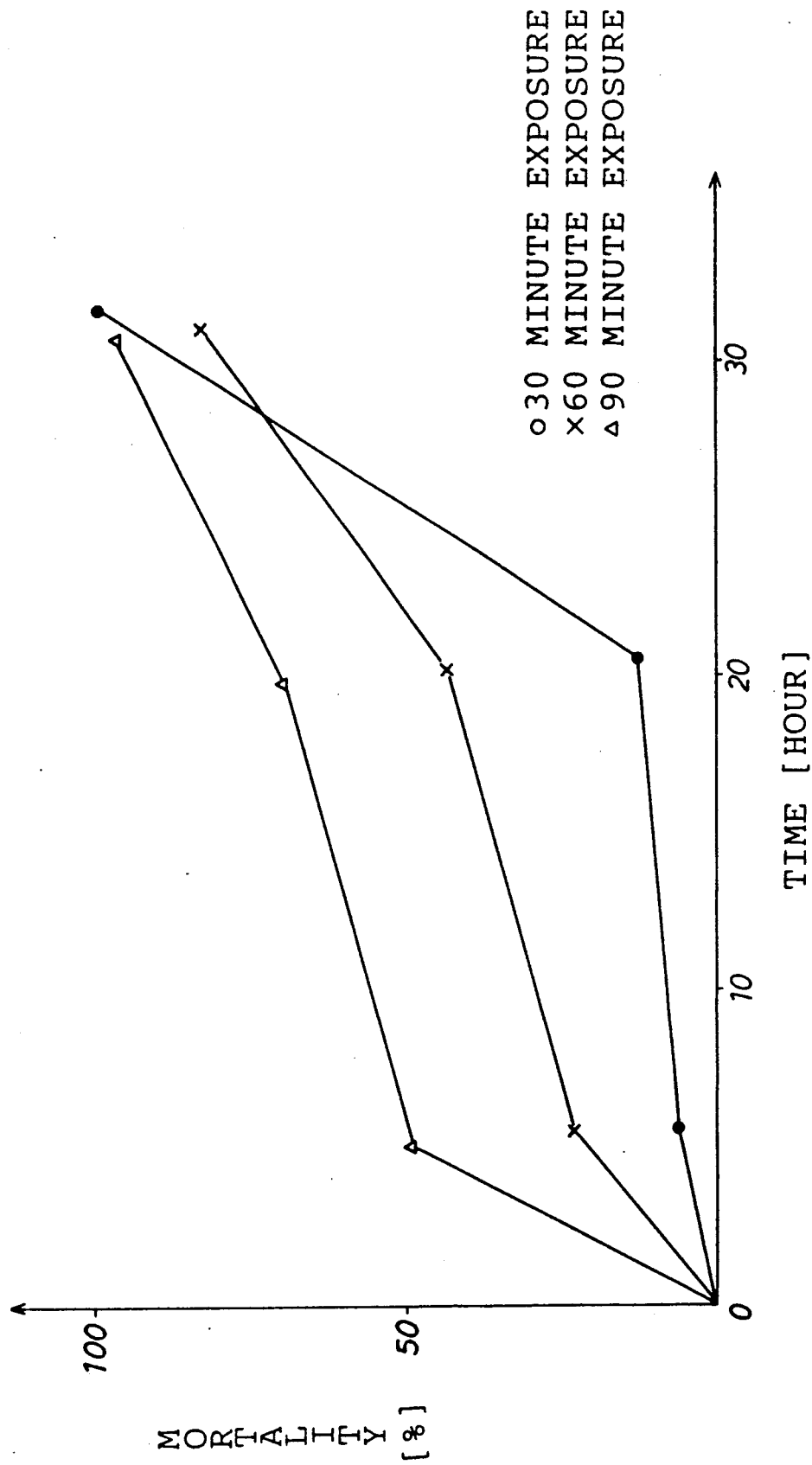
FIG. 5 is a graph showing the relationship between the mortality of coptotermes and time after the exposure of the coptotermes to Home gels containing 0.05% of fine particles for thirty to ninety minutes.
Figure 6:
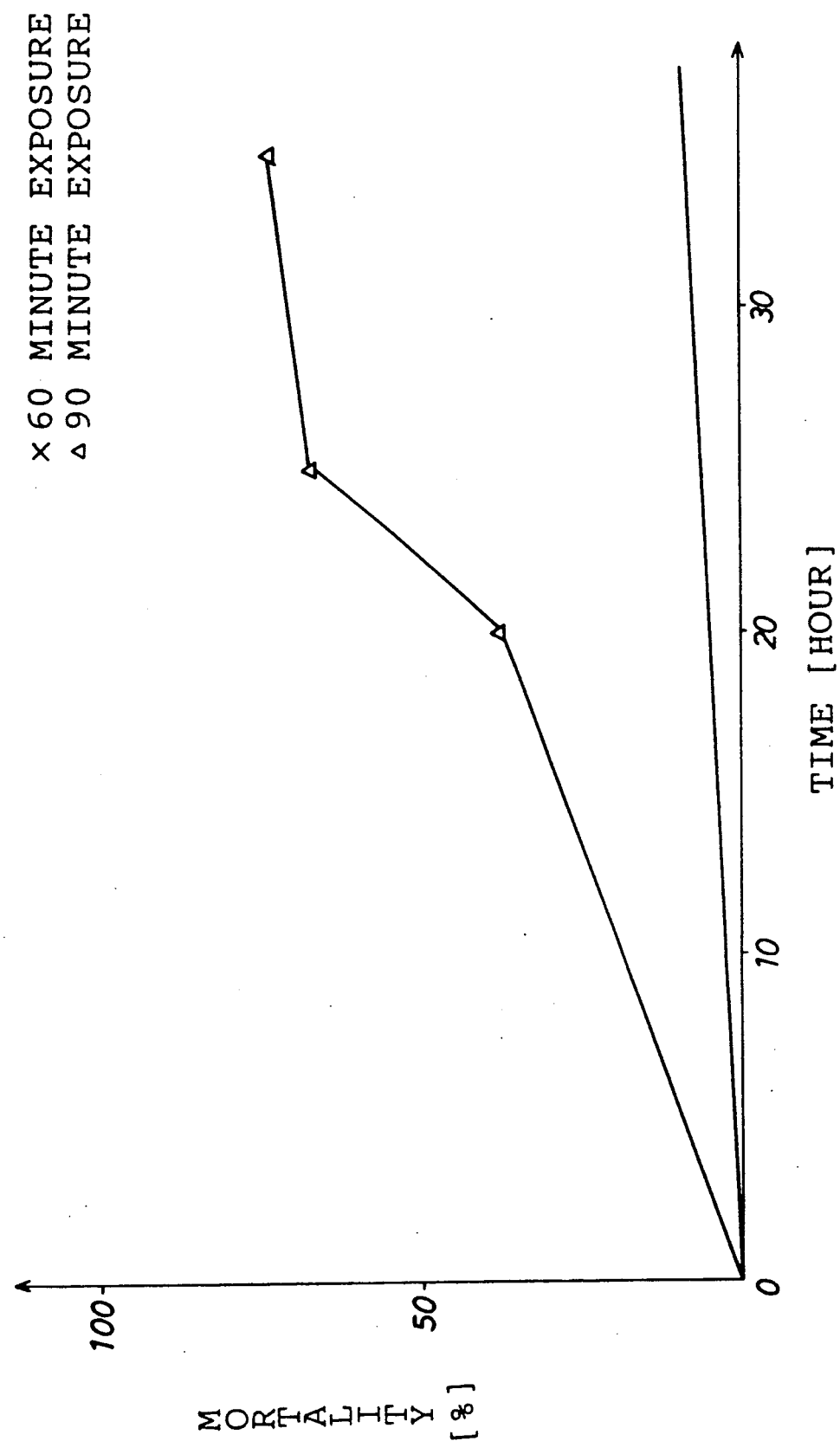
FIG. 6 is a graph showing the relationship between the mortality of coptotermes and time after the exposure of the coptotermes to Home gels containing 0.01% to 0.03% of fine particles for sixty to ninety minutes.
Figure 8:
FIGS. 8–12 are microphotographs of coptotermes' body portions (enlarged one thousand to three thousand times)
Figure 10:
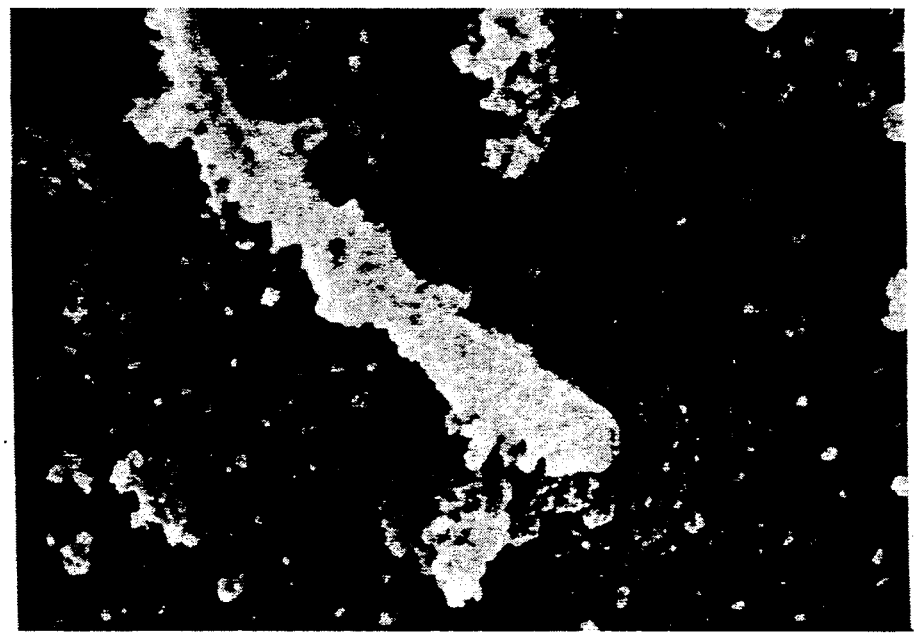
Figure 12:
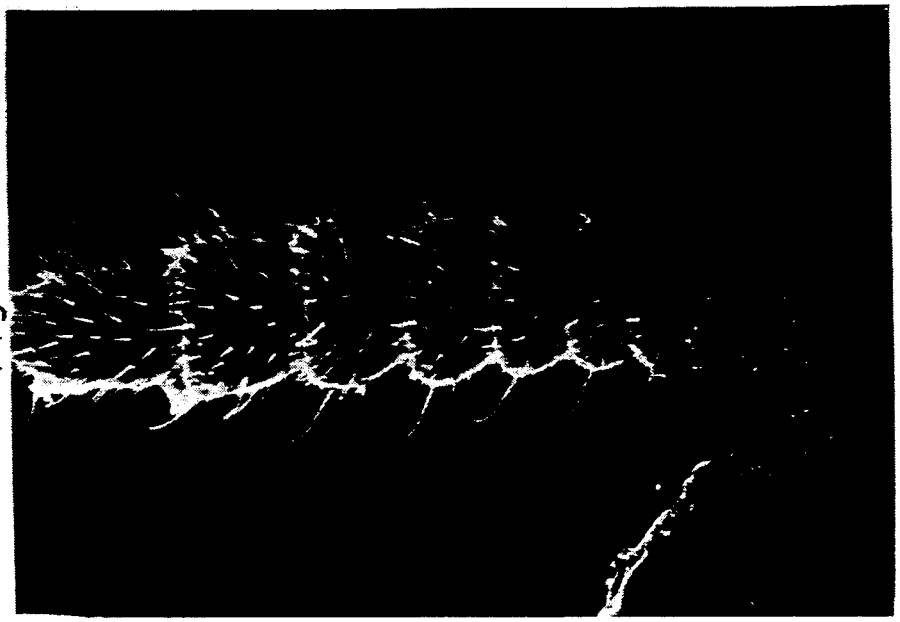
Figure 13:
FIGS. 13 and 14 are photographs of coptotermes after the exposure to the silica gels.
Figure 14:
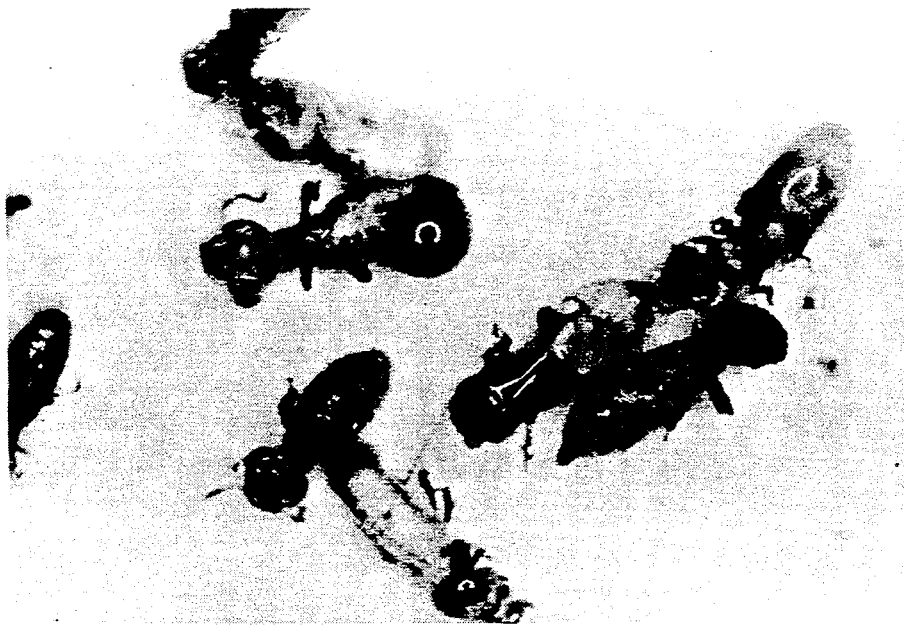

As shown in FIGS. 4–6, when the termites are exposed to the silica-gel particles for a long time, the mortality of termites increases. In FIG. 5, the silica gels are filtered with a 50μm filter to obtain the silica-gel particles with a diameter of 50μm maximum, and the silica-gel particle diameter distribution is shown in FIG. 1. Comparing FIG. 5 and FIG. 6 which differ in the silica-gel particle diameter, when the percentage of the fine particles with the diameter of 50μm maximum contained in the silica gels increases, the mortality of termites increases, accordingly. After the exposure of coptotermes to the silica gels, the hind leg of the one shown in FIG. 8 is covered with the silica-gel particles as shown in FIG. 9, its body surface changes as shown in FIG. 10, and its antenna shown in FIG. 11 changes as shown in FIG. 12. After coptotermes are exposed to the silica-gel particles, they first partially turn black as shown in FIG. 13. Subsequently, they almost completely turn black as shown in FIG. 14, and finally die.

Figure 7:
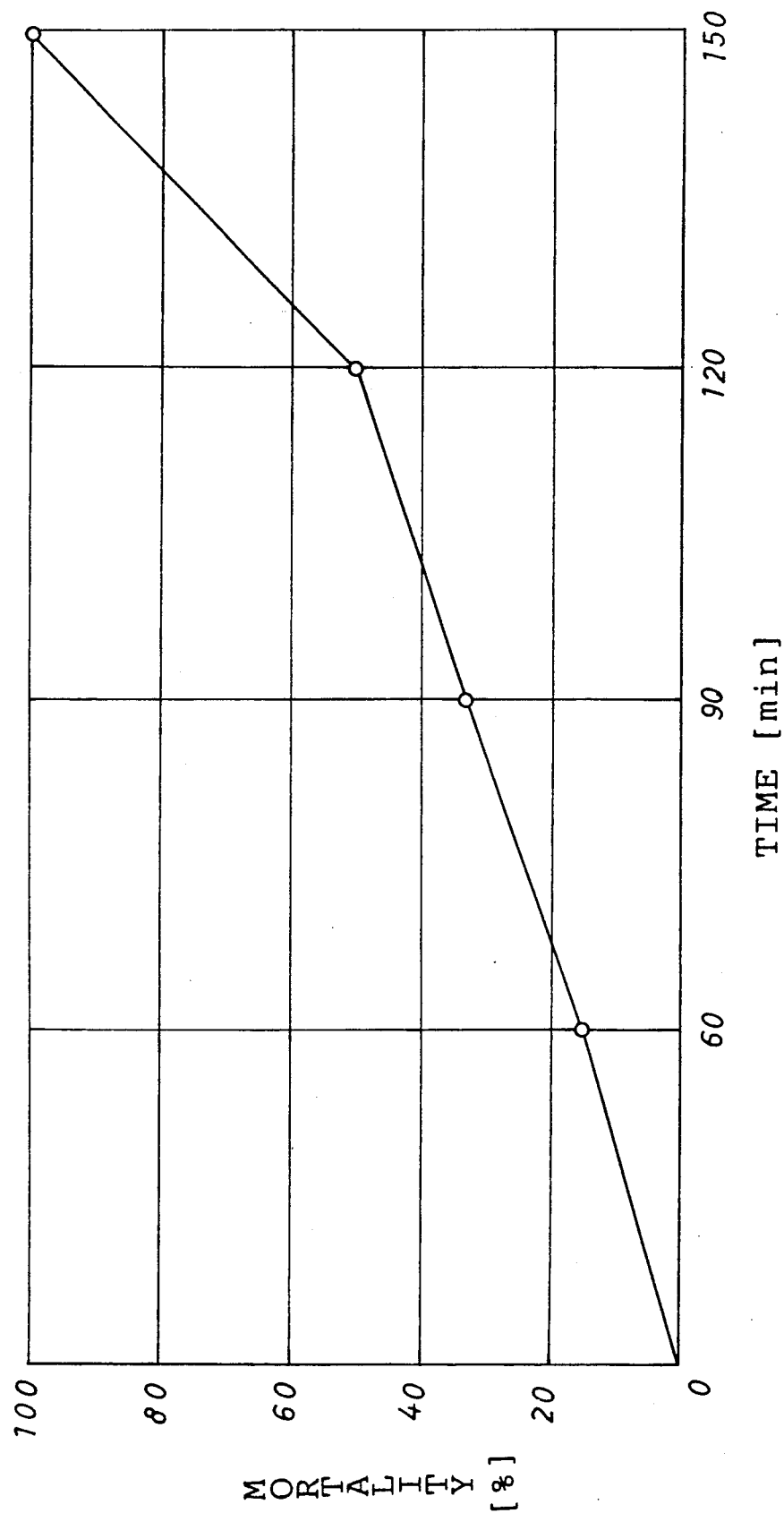
FIG. 7 is a graph showing the relationship between the mortality of Tyrophagus putrescentiae and time after exposure to the silica gels at the relative humidity of 70%.

The silica gels of this embodiment exert the lethal effect on the insect pests other than termites, such as Tyrophagus putrescentiae as shown in FIG. 7.

In this embodiment, humidity-controlling silica gels, an adsorbent drying agent, and Home gel refer to the same silica gels. Various types of the adsorbent drying agent are available. Even the adsorbent drying agent that is provided with the properties other than specified in this embodiment can control termites.

This is just one embodiment of the present invention. The claim is not limited by any of the details of this description, and should be construed broadly within its general principles.

What is claimed is:

1. A biotically non-toxic composition for killing insect pests, consisting essentially of silica gel having a minimum particle diameter of 350μm, and about 0.05% to about 5% by weight silica particles having a maximum diameter of 50μm.

* * * * *

UNITED STATES PATENT AND TRADEMARK OFFICE
CERTIFICATE OF CORRECTION

PATENT NO. : 5,135,750
DATED : August 4, 1992
INVENTOR(S) : Yoshito NAKASHIMA

Figure 11:
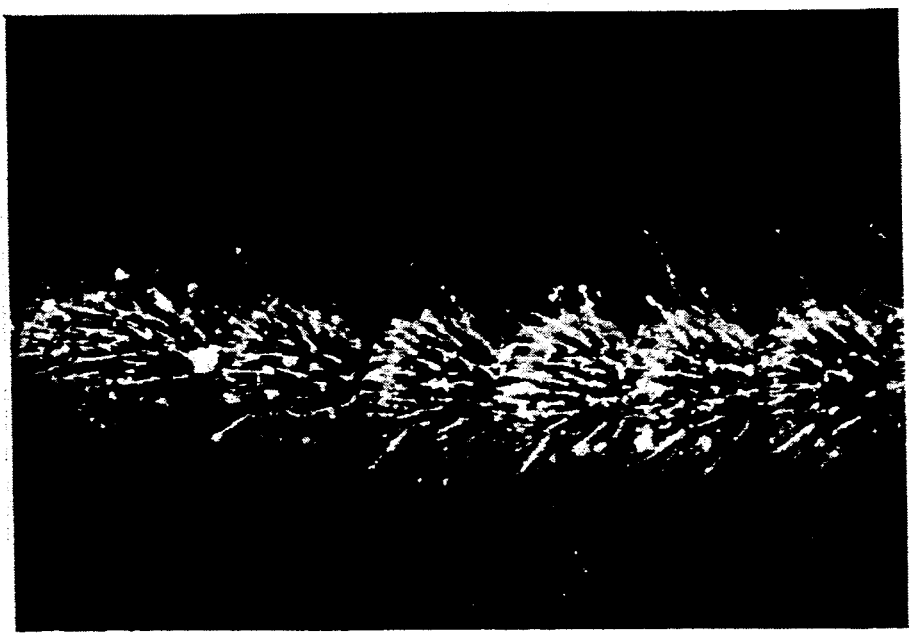

It is certified that error appears in the above-identified patent and that said Letters Patent is hereby corrected as shown below:

IN THE DRAWINGS:

Sheet 10 of 11, change "Fig. 12" to --Fig. 11--;

change "Fig. 11" to --Fig. 12--.

Signed and Sealed this

Twenty-first Day of December, 1993

Attest:

BRUCE LEHMAN

Attesting Officer      Commissioner of Patents and Trademarks